(12) United States Patent
Clark et al.

(10) Patent No.: US 8,006,558 B2
(45) Date of Patent: Aug. 30, 2011

(54) MEASURING A SAMPLE

(75) Inventors: Matthew Clark, Nottingham (GB);
Stephen Sharples, Nottingham (GB)

(73) Assignee: The University of Nottingham,
Nottingham (GB)

( * ) Notice: Subject to any disclaimer, the term of this
patent is extended or adjusted under 35
U.S.C. 154(b) by 717 days.

(21) Appl. No.: 11/994,779

(22) PCT Filed: Jul. 6, 2006

(86) PCT No.: PCT/GB2006/002504
§ 371 (c)(1),
(2), (4) Date: Mar. 4, 2008

(87) PCT Pub. No.: WO2007/003952
PCT Pub. Date: Jan. 11, 2007

(65) Prior Publication Data
US 2008/0163690 A1    Jul. 10, 2008

(30) Foreign Application Priority Data

Jul. 6, 2005 (GB) .................................. 0513756.7

(51) Int. Cl.
*G01N 29/07* (2006.01)
(52) U.S. Cl. ................. 73/597; 73/602; 73/626; 73/655
(58) Field of Classification Search .................. 73/597,
73/602, 655, 656, 657, 625, 626; 356/357,
356/358
See application file for complete search history.

(56) References Cited

U.S. PATENT DOCUMENTS

| 5,410,371 | A  | * | 4/1995 | Lambert | 348/769 |
| 5,801,312 | A  | * | 9/1998 | Lorraine et al. | 73/602 |
| 6,182,512 | B1 | * | 2/2001 | Lorraine | 73/655 |
| 6,877,376 | B1 | * | 4/2005 | Schuster et al. | 73/602 |
| 6,945,114 | B2 | * | 9/2005 | Kenderian et al. | 73/643 |
| 7,150,193 | B2 | * | 12/2006 | Lorraine et al. | 73/597 |
| 7,716,987 | B2 | * | 5/2010 | Sathish et al. | 73/589 |
| 2002/0100326 | A1 | * | 8/2002 | Stein | 73/597 |

FOREIGN PATENT DOCUMENTS

GB         2 311 858        10/1997

OTHER PUBLICATIONS

Clark, Matt et al., "Non-Contact Acoustic Microscopy", Meas. Sci. Technol., vol. 11, No. 12, Dec. 1, 2000, pp. 1792-1801.

(Continued)

*Primary Examiner* — Jacques M Saint Surin
(74) *Attorney, Agent, or Firm* — Nixon & Vanderhye P.C.

(57) ABSTRACT

A sample 10 is measured by generating ultrasound at 12, for example by using a laser 22 and spatial light modulator 26. The ultrasound is detected at 16, for example by optical beam deflection techniques. A characteristic of the generation at 12 is swept across a range of values to vary the efficiency of generation of ultrasound. The value of the characteristic, which corresponds with the peak amplitude detected at 16, is identified to provide a measure of the acoustic velocity at the region 12. The method is executed at a plurality of sites 12, 20 to provide a set of spatially resolved measurements of the sample 10. This allows an image of the sample to be created.

34 Claims, 2 Drawing Sheets

OTHER PUBLICATIONS

Hong, Yi et al., "Rapid and Accurate Analysis of Surface and Pseudo-Surface Waves Using Adaptive Laser Ultrasound Techniques", Ultrasonics, vol. 42, No. 1-9, Apr. 2004, pp. 515-518.

Nishino, Hideo et al., "Optical Probe Detection of High-Frequency Surface Acoustic Waves Generated by Phase Velocity Scanning of Laser Interference Fringes", Jpn. J. Appl. Phys., vol. 33, No. 5B, 1994, pp. 3260-3264.

Sharples, Steve D. et al., "All-Optical Adaptive Scanning Acoustic Microscope", Ultrasonics, vol. 41, No. 4, Jun. 2003, pp. 295-299.

Hong, Y. et al., "Rapid Measurement of Surface Acoustic Wave Velocity on Single Crystals Using an All-Optical Adaptive Scanning Acoustic Microscope", Applied Physics Letters, vol. 83, No. 16, Oct. 20, 2003, pp. 3260-3262.

* cited by examiner

MEASURING A SAMPLE

This application is the U.S. National Phase of International Application No. PCT/GB2006/002504 filed 6 Jul. 2006 which designated the U.S. and claims priority to Great Britain Patent Application No. 0513756.7 filed 6 Jul. 2005, the entire contents of each of which are hereby incorporated by reference.

The present invention relates to sample measurement and, in particular, to sample measurement by acoustic techniques.

Acoustic techniques have been proposed for obtaining information about the make-up of the microstructure of materials, particularly multi-grained structures such as titanium alloys and aluminium, which is of great interest to many in industries such as aerospace. The ability to map the material microstructure—in effect to image the grains—quickly and in a nondestructive manner is useful from both a process control perspective and in the area of nondestructive evaluation.

One method of imaging the grain microstructure is through the use of scanning acoustic microscopy with the V(z) method. This is described by R. A. Lemons and C. F. Quate in "Acoustic microscope—scanning version" (Applied Physics Letters, 24:163-165, 1974). This technique provides a method for indirectly measuring a function of the ultrasonic velocity, in turn related to the material microstructure. However, this method suffers from being intrinsically a contact method and the process of contact perturbs the measurement. It is also slow and has variable spatial resolution that depends on the local velocity.

Another acoustic method measures the slowness surface of single crystal materials. This is described by C. B. Scruby and L. E. Drain in "Laser Ultrasonics, Techniques and Applications" (Adam Hilger, Bristol, U.K., 1990). However, the technique has no spatial resolution. Further, it is slow.

Examples of the present invention provide a method of measuring a sample, in which:

an acoustic wave is generated in the sample;

the generated wave is detected;

generation is effected at a plurality of values of a characteristic of generation, to vary the efficiency of generation, the detected wave is measured to identify the efficiency of generation at each value of the characteristic, thereby to provide a measurement of the acoustic velocity at the generation site, and the aforesaid steps are executed at a plurality of generation sites on the sample, to provide a set of spatially resolved measurements of the sample.

The set of measurements may be processed to provide an image of the sample.

In another aspect, examples of the invention provide a method of generating an image of a sample, in which:

an acoustic wave is generated in the sample;

the generated wave is detected;

generation is effected at a plurality of values of a characteristic of generation, to vary the efficiency of generation, the detected wave is measured to identify the efficiency of generation at each value of the characteristic, thereby to provide a measurement of the acoustic velocity at the generation site, and the method is executed at a plurality of generation sites on the sample, to provide a set of spatially resolved measurements of the sample, which are processed to provide an image of the sample.

In either aspect, each measurement may be processed to provide a corresponding region of the image. Each region of the image may be given an appearance selected from a range of appearances, in accordance with the measurement at the corresponding generation site. Each region of the image may be coloured or shaded, the colour or shade being selected from a spectrum or range which represents a range of acoustic velocities.

The value of the characteristic may be swept across a range, to effect generation at the plurality of values. Alternatively, generation may be effected simultaneously at a plurality of values. The plurality of values may form a continuum or be discrete.

The amplitude of the wave may be detected.

The acoustic velocity at each generation site may be calculated from the value which corresponds with the peak detected amplitude. The characteristic may be the frequency of generation. The characteristic may be the wavenumber of generation.

The acoustic wave may be generated by illuminating the sample with spatially modulated light. The temporal frequency of the illuminating light intensity may be swept. The spatial modulation of the illuminating light may be swept.

The measurement at each value may be compared with a set of data representing an expected profile of measurements.

The plurality of generation sites may be regularly spaced.

The acoustic wave may be ultrasonic.

Examples of the present invention also provide apparatus for measuring a sample, comprising:

an acoustic wave generator for generating an acoustic wave in the sample, and a detector for detecting the generated wave, the generator being operable to effect generation at a plurality of values of a characteristic of generation to vary the efficiency of generation, and the detector being operable to measure the detected wave to identify the efficiency of generation at each value of the characteristic, thereby to provide a measurement of the acoustic velocity at the generation site, and the apparatus is operable to obtain measurements at a plurality of generation sites on the sample, to provide a set of spatially resolved measurements of the sample.

The detector may be operable to process the set of measurements to provide an image of the sample.

In another aspect, examples of the invention provide apparatus for generating an image of a sample, comprising:

an acoustic wave generator for generating an acoustic wave in the sample, and a detector for detecting the generated wave, the generator being operable to effect generation at a plurality of values of a characteristic of generation to vary the efficiency of generation, and the detector being operable to measure the detected wave to identify the efficiency of generation at each value of the characteristic, thereby to provide a measurement of the acoustic velocity at the generation site, and the apparatus is operable to obtain measurements at a plurality of generation sites on the sample, to provide a set of spatially resolved measurements of the sample, and to process the measurements to provide an image of the sample.

In either aspect, the apparatus may process each measurement to provide a corresponding region of the image. Each region of the image may be given an appearance selected from a range of appearances, in accordance with the measurement at the corresponding generation site. Each region of the image may be coloured or shaded, the colour or shade being selected from a spectrum or range which represents a range of acoustic velocities.

The generator may be operable to sweep the value of the characteristic across a range, to effect generation at the plurality of values. Alternatively, the generator may effect simultaneous generation at the plurality of values. The plurality of values may form a continuum or be discrete.

The detector may be operable to detect the amplitude of the wave.

The detector may calculate the acoustic velocity at each generation site from the value which corresponds with the peak detected amplitude. The generator may generate at a plurality of frequencies. The generator may generate at a plurality of wavenumbers.

The generator may generate the acoustic wave by illuminating the sample with spatially modulated light. The generator may sweep the temporal frequency of the illuminating light intensity. The generator may sweep the spatial modulation of the illuminating light.

The detector may measure at each value by comparing measurements with a set of data representing an expected profile of measurements.

The plurality of generation sites may be regularly spaced.

The generator may generate an ultrasonic acoustic wave.

Examples of the invention will now be described in more detail, by way of example only, and with reference to the accompanying drawings, in which.

Figure 1:
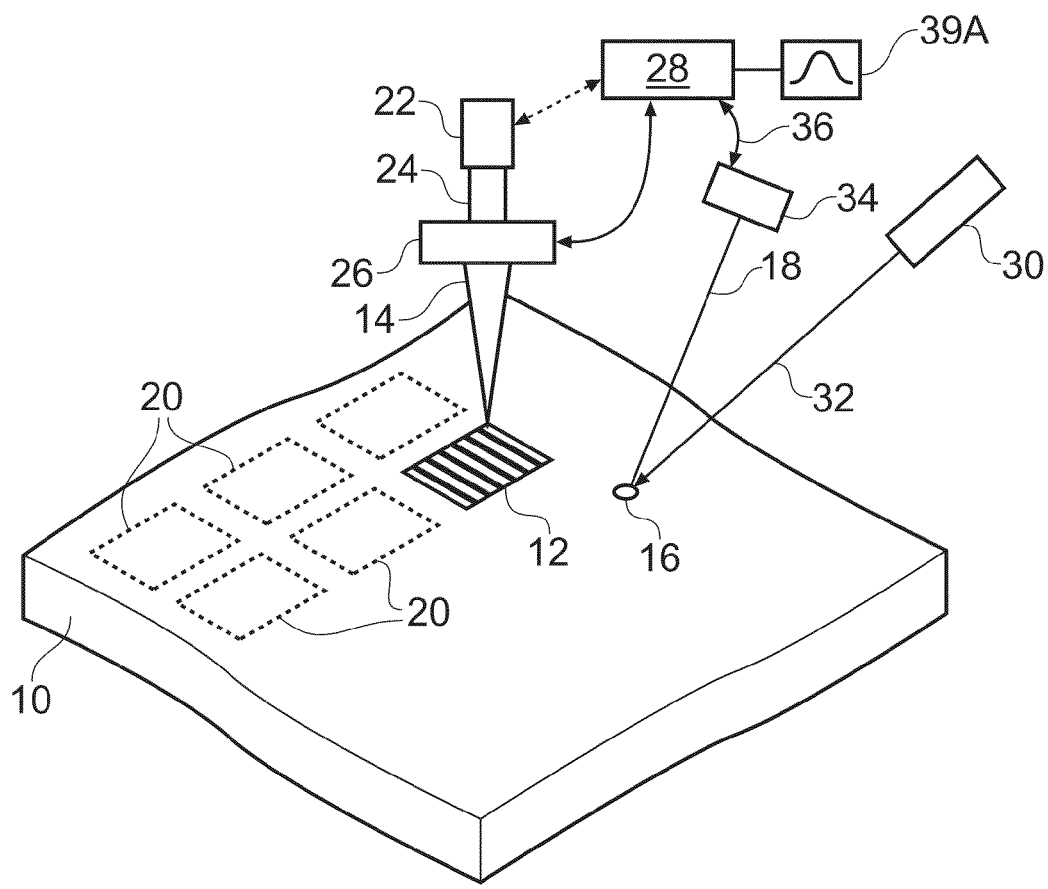
FIG. 1 is a schematic diagram of an example implementation of the invention.

Turning to FIG. 1, the diagram shows a sample 10 to be measured. There is an ultrasound generation region 12, at which an ultrasound generation signal 14 generates ultrasound within the sample 10, as will be described. An ultrasound detection region 16 results in a detection signal 18, as will be described. As will be described, generation is effected at 12 at a plurality of values of a characteristic of generation, to vary the efficiency of generation. The detected wave is measured to identify the efficiency of generation at each value of the characteristic, thereby to provide a measure of the acoustic velocity at the region 12. This method is executed at a plurality of generation sites 12, 20 to provide a set of spatially resolved measurements of the sample 10.

In more detail, generation at the region 12 results from illumination by the output of a light source 22. In one example, this may be a pulsed laser such as a Nd-YAG laser operating at 1064 nm wavelength. The laser output 24 is treated by a spatial light modulator 26 (SLM). An SLM is a device, known in itself, which contains a large array of pixels whose properties can be individually changed by a control arrangement 28, to produce various images. In this example, the SLM is used to produce an image of alternating light and dark lines at the region 12, on the surface of the sample 10 under investigation. Applying an image consisting of lines (as illustrated in FIG. 1) allows ultrasound to be generated, which travels perpendicular to the direction of the lines. The efficiency with which ultrasound is generated depends upon the line spacing and temporal frequency of illumination intensity, that is, the pulse frequency with which pulses of 1064 nm light are produced by the laser 22. If the pulsed laser 22 has a fixed pulse frequency f, then for a given number of lines, the largest amplitude ultrasonic wave that can be generated occurs when $$\lambda = 2\pi k \quad (1)$$

where $\lambda$ is the separation between the lines and k is the wavenumber of the generated ultrasound. Alternatively, if $\lambda$ is fixed, then the largest amplitude ultrasonic wave that can be generated occurs when $$f = Ck/2\pi \quad (2)$$

where C is the acoustic velocity given by the well known relationship:

$$C = 2\pi f/k \quad (3)$$

An SLM device 26 allows the image on the sample 10 to be changed rapidly. Thus, a series of images of pulsed laser light 24 can be created on the sample 10, each with different line spacings but located at the same position 12, and with a constant pulse frequency. This is equivalent to sweeping the wavenumber characteristic of the generation, to vary the efficiency with which ultrasound is generated, as noted above. Other methods for varying the wavelength or wavenumber may be used.

In a further example, the laser 22 may be a laser which can be controlled to change the pulse frequency. This allows the temporal frequency of the illuminating light intensity to be the characteristic of generation which is swept across a range of values, thus allowing the efficiency with which ultrasound is generated to be varied, again as noted above.

In the example illustrated in FIG. 1, the SLM device 26 is controlled by the control arrangement 28, allowing $\lambda$ to be swept. In an alternative, the control arrangement 28 may control the laser 22, allowing the temporal frequency f to be swept.

In other examples, generation at a plurality of values of a generation characteristic may be simultaneous, for example by illuminating a fixed line spacing with a broadband excitation source.

The ultrasound generated at 12 is detected at 16 on the sample 10, using any of the well-known suitable methods for detecting ultrasound. Examples include laser-based techniques such as optical beam deflection or interferometry. In the instrument built to demonstrate the technique, optical beam deflection is used. This is illustrated schematically as illumination of the region 16 by a beam 32 from a second source 30, resulting in the reflected beam 18, which is incident on a detector 34. The incidence of an ultrasonic wave at the region 16 causes changes in the deflection of the beam 32, which is measured as a change in the signal strength detected at 34.

The output of the detector 34 is provided to the control 28 at 36, allowing the detector output to be correlated with the corresponding value of the characteristic at the generation region 12.

In the example being described, the laser 22 and SLM device 26 form a spatially small, high-Q/narrow-band source of ultrasound, which is used to generate an ultrasonic wave in the sample. The source 30 and detector 34 provide a wideband (or tunable) ultrasound detector. In this example, either the wavenumber, k, of the ultrasound, at a fixed pulse frequency f is swept or the pulse frequency, f, is swept at a fixed wavenumber, as has been described. During this sweep the ultrasound signal is detected by the broadband ultrasound detector and recorded by the controller 28. The amplitude output of the ultrasound detector is signal processed within the controller 28 to extract a graph of amplitude with wavenumber or amplitude with frequency. The maximum of this graph gives the optimum wavenumber value (for the current frequency f) or frequency value (for the current wavenumber value k). The optimum value is then converted into an acoustic velocity measurement, C using the relationship (3).

Figure 2:
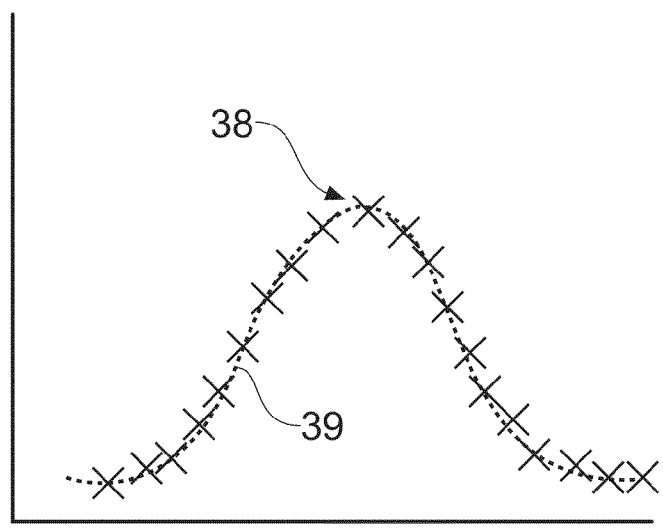
FIG. 2 is a diagram of data retrieved and processed within the arrangement of FIG. 1.

FIG. 2 represents the data taken at one point on the sample 10. The vertical axis represents the magnitude of the measured ultrasonic amplitude. The horizontal axis represents the value of the characteristic, i.e. the wavenumber k or the frequency f. Data points are illustrated by diagonal crosses on FIG. 2. It can be seen that these form a curve having a clear peak at 38. The value of the characteristic (i.e. the horizontal axis value) at the peak 38 is the value used to derive the acoustic velocity measurement, C, for the current position of the generation region 12. Thus, it is the process of forming an acoustic spectrum at the region 12, in this example by sweeping the wavenumber or frequency to create the plot shown in FIG. 2, which represents the extraction of the single data point used to calculate the velocity at the measurement point 12.

In the alternative in which broadband excitation is used, the detector detects the entirety of the ultrasonic signal. Appropriate signal processing techniques are used to identify the frequency at which generation was most efficient which corresponds with the frequency of the peak 38, which again corresponds with extracting a single data point.

It can be seen in FIG. 2 that a curve 39 is superimposed on the collected data points. This curve may represent an expected profile of measurements, to assist in identifying abnormal measurements, or otherwise assisting in signal processing to identify the position of the peak 38. Data representing the curve 39 may be stored at 39a, for access by the control arrangement 28.

We have realised that if the region 12 is sufficiently small, each different position 12, 20 will have a single characteristic phase velocity C. Measuring a characteristic of the generation at a plurality of values, in the manner described, (for example by sweeping the line spacing for a fixed temporal illumination frequency, or sweeping the temporal illumination frequency for a fixed line spacing) allows the local characteristic phase velocity C to be measured from the peak amplitude 38. Furthermore, we have realised that the position of the detection region 16, relative to the generation region 12, is arbitrary, so long as it remains constant during a set of readings used to create a plot as shown in FIG. 2. This is because the position of the peak 38 (in the domain of the characteristic) is not affected by perturbations created within the sample 10, between the region 12 and the region 16, and is therefore not affected by the position of the region 16, relative to the region 12. These perturbations may affect the height of the peak 38 and the shape of the peak, but not the position.

Once a value for the acoustic velocity C has been derived for a particular region 12, by taking a spectrum of readings in the manner described above, the measured acoustic velocity is recorded by the control arrangement 28 as the value corresponding with the current location 12. Relative movement between the sample 10 and the laser 22 and SLM device 26 then allows an alternative generation site 20 to be illuminated. A new measurement is then produced in the same manner by scanning the characteristic of generation to create a plot as shown in FIG. 2, and then to determine an acoustic velocity from the position of the peak 38. The new measurement corresponds with the generation site 20. Repeatedly executing the method in this manner allows acoustic velocity measurements to be made at a plurality of generation sites, which may be regularly spaced across the sample 10.

Figure 3:
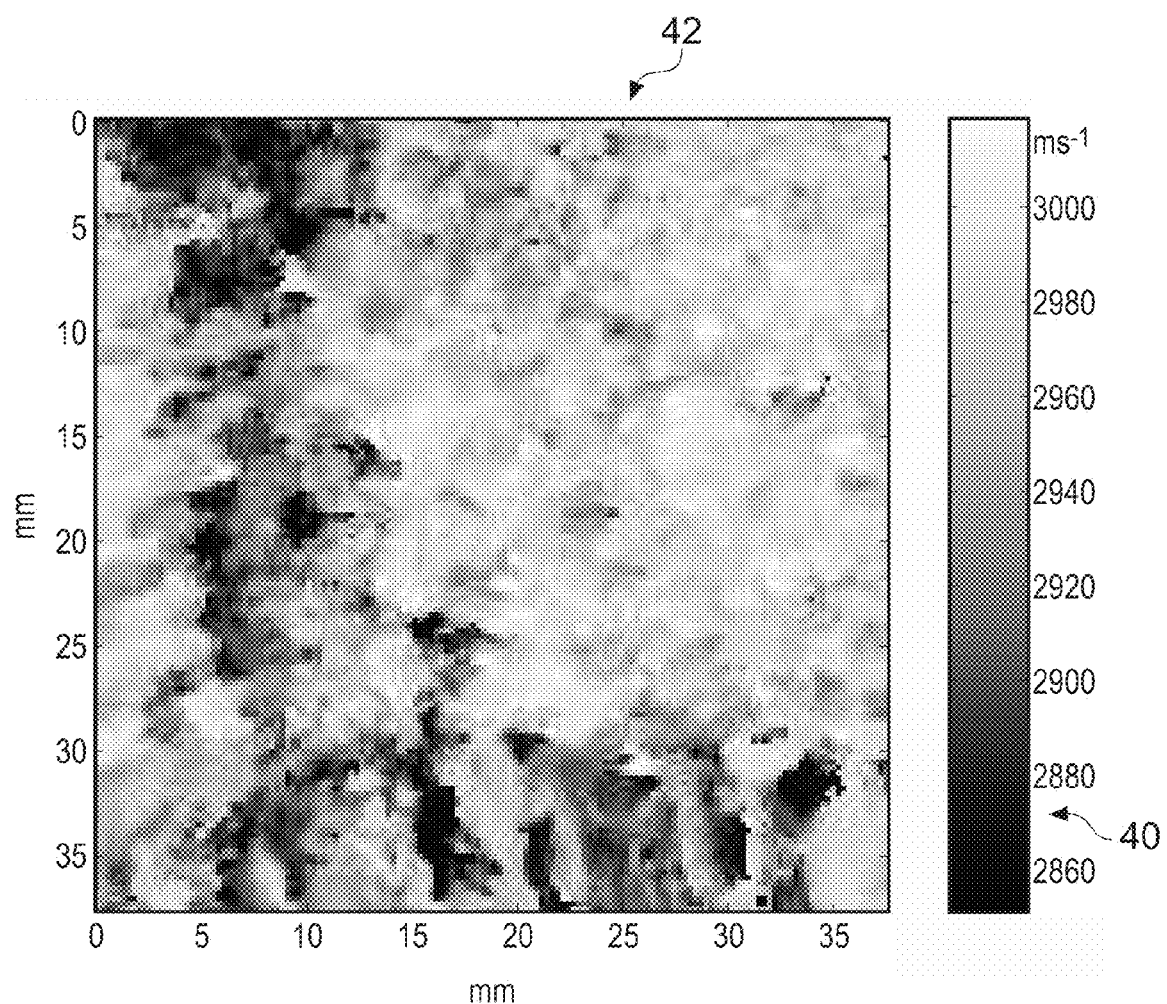
FIG. 3 is an illustrative example of an image provided by the arrangements of FIG. 1.

Once the desired set of acoustic velocity measurements have been made from the generation sites 20, the control arrangement 28 may further process these to provide output in the form of an image. In an example, each measurement is processed to provide a corresponding region of the image by colouring or shading that image region in accordance with a spectrum of colours or range of densities, chosen to represent a corresponding range of acoustic velocities. FIG. 3 illustrates an example of an image so formed. The density of shading at any particular point on the image of FIG. 3 can be converted to a velocity value by the grey scale 40. This allows a human user to obtain numerical measurement values from the image. However, we envisage that pictorial representation of the acoustic velocity measurements, in the manner illustrated in FIG. 3, will allow a user to assess a sample quickly, by eye. For example, in FIG. 3, it can be seen that the acoustic velocities are generally higher (lighter shading) toward the upper right corner of the image, than they are along the lower edge or left hand edge of the image. This indicates differences in the sample 10, which may arise, for example, from different crystal states, crystallographic orientations, faults, impurities, grain size variations or in other ways.

It can be seen from the above description that the examples described make use of acoustic waves generated and detected by lasers and are therefore wholly non-contact and non-destructive. The techniques described can be implemented relatively quickly and can, in principle, be used with samples of unlimited size. The wholly non-contact nature of the technique removes the possibility of perturbations arising from coupling arrangements commonly found in ultrasonic systems.

The techniques described are not restricted to use in multi-grain materials, and can be used to obtain spatial information which exists for other reasons, such as spatial variation in material thickness, spatial variation in coating thickness, and the like.

The above example has referred to optical beam deflection as the detection technique. Other detection techniques could be used, such as Fabry-Perot interferometry, Michelson interferometry, laser vibrometers or other non-optical techniques, or other types of transducers. Other arrangements for creating acoustic waves could be used.

The signal processing described above extracts information from the position of the peak 38. Other information may be available, for example from the width of the peak. In some circumstances, multiple peaks may arise, according to the thickness of the sample, and the separation of the multiple peaks may provide useful information, such as a measurement of sample thickness.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A method of measuring a sample, in which:
    an acoustic wave is generated in the sample;
    the generated wave is detected;
    generation is effected at a plurality of values of a frequency of generation, to vary the efficiency of generation,
    the detected wave is measured to identify the efficiency of generation at each value of the frequency of generation, thereby to provide a measurement of the acoustic velocity at the generation site,
    and the aforesaid steps are executed at a plurality of generation sites on the sample, to provide a set of spatially resolved measurements of the sample.

2. A method according to claim 1, wherein the set of measurements are processed to provide an image of the sample.

3. A method according to claim 2, wherein each measurement is processed to provide a corresponding region of the image.

4. A method according to claim 3, wherein each region of the image is given an appearance selected from a range of appearances, in accordance with the measurement at the corresponding generation site.

5. A method according to claim 4, wherein each region of the image is coloured or shaded, the colour or shade being selected from a spectrum or range which represents a range of acoustic velocities.

6. A method according to claim 1, wherein the value of the frequency of generation is swept across a range, to effect generation at the plurality of values.

7. A method according to claim 1, wherein generation is effected simultaneously at a plurality of values.

8. A method according to claim 1, wherein the plurality of values form a continuum.

9. A method according to claim 1, wherein the plurality of values are discrete.

10. A method according to claim 1, wherein the amplitude of the wave is detected.

11. A method according to claim 10, wherein the acoustic velocity at each generation site is calculated from the value which corresponds with the peak detected amplitude.

12. A method according to claim 1, wherein the acoustic wave is generated by illuminating the sample with spatially modulated light.

13. A method according to claim 12, wherein the temporal frequency of the illuminating light intensity is swept.

14. A method according to claim 1, wherein the measurement at each value is compared with a set of data representing an expected profile of measurements.

15. A method according to claim 1, wherein the plurality of generation sites are regularly spaced.

16. A method according to claim 1, wherein the acoustic wave is ultrasonic.

17. A method of generating an image of a sample, in which:
an acoustic wave is generated in the sample;
the generated wave is detected;
generation is effected at a plurality of values of a frequency of generation, to vary the efficiency of generation,
the detected wave is measured to identify the efficiency of generation at each value of the frequency of generation, thereby to provide a measurement of the acoustic velocity at the generation site,
and the method is executed at a plurality of generation sites on the sample, to provide a set of spatially resolved measurements of the sample, which are processed to provide an image of the sample.

18. Apparatus for measuring a sample, comprising:
an acoustic wave generator for generating an acoustic wave in the sample, and
a detector for detecting the generated wave,
the generator being operable to effect generation at a plurality of values of a frequency of generation to vary the efficiency of generation,
and the detector being operable to measure the detected wave to identify the efficiency of generation at each value of the frequency of generation, thereby to provide a measurement of the acoustic velocity at the generation site,
and the apparatus is operable to obtain measurements at a plurality of generation sites on the sample, to provide a set of spatially resolved measurements of the sample.

19. Apparatus according to claim 18, further comprising a control arrangement operable to process the set of measurements to provide an image of the sample.

20. Apparatus according to claim 19, wherein the apparatus processes each measurement to provide a corresponding region of the image.

21. Apparatus according to claim 19, wherein each region of the image is given an appearance selected from a range of appearances, in accordance with the measurement at the corresponding generation site.

22. Apparatus according to claim 21, wherein each region of the image is coloured or shaded, the colour or shade being selected from a spectrum or range which represents a range of acoustic velocities.

23. Apparatus according to claim 18, wherein the generator is operable to sweep the value of the frequency of generation across a range, to effect generation at the plurality of values.

24. Apparatus according to claim 18, wherein the generator is operable to effect simultaneous generation at the plurality of values.

25. Apparatus according to claim 18, wherein the plurality of values form a continuum.

26. Apparatus according to claim 18, wherein the plurality of values are discrete.

27. Apparatus according to claim 18, wherein the detector is operable to detect the amplitude of the wave.

28. Apparatus according to claim 18, wherein the generator is operable to generate at a plurality of wavenumbers.

29. Apparatus according to claim 18, wherein the generator generates the acoustic wave by illuminating the sample with spatially modulated light.

30. Apparatus according to claim 18, wherein the generator sweeps, in use, the temporal frequency of the illuminating light intensity.

31. Apparatus according to claim 18, further comprising a control arrangement operable to measure at each value by comparing measurements with a set of data representing an expected profile of measurements.

32. Apparatus according to claim 18, wherein the plurality of generation sites is regularly spaced.

33. Apparatus according to claim 18, wherein the generator is operable to generate an ultrasonic acoustic wave.

34. Apparatus for generating an image of a sample, comprising:
an acoustic wave generator for generating an acoustic wave in the sample, and
a detector for detecting the generated wave,
the generator being operable to effect generation at a plurality of values of a frequency of generation to vary the efficiency of generation,
and the detector being operable to measure the detected wave to identify the efficiency of generation at each value of the frequency of generation, thereby to provide a measurement of the acoustic velocity at the generation site,
and the apparatus is operable to obtain measurements at a plurality of generation sites on the sample, to provide a set of spatially resolved measurements of the sample, and to process the measurements to provide an image of the sample.

* * * * *